(«12») United States Patent
Eiger (10) Patent No.: US 9,138,586 B2
(45) Date of Patent: Sep. 22, 2015

(54) CONTACT BLOCK USING SPHERICAL ELECTRICAL CONTACTS FOR ELECTRICALLY CONTACTING IMPLANTABLE LEADS

(75) Inventor: Jay H. Eiger, Eastlake, OH (US)

(73) Assignee: GREATBATCH LTD., Clarence, NY (US)

( * ) Notice: Subject to any disclaimer, the term of this patent is extended or adjusted under 35 U.S.C. 154(b) by 0 days.

(21) Appl. No.: 13/359,861

(22) Filed: Jan. 27, 2012

(65) Prior Publication Data

US 2013/0197603 A1   Aug. 1, 2013

(51) Int. Cl.
| | |
|---|---|
| *A61N 1/375* | (2006.01) |
| *H01R 13/02* | (2006.01) |
| *H01R 13/514* | (2006.01) |
| *H01R 13/52* | (2006.01) |
| *A61N 1/36* | (2006.01) |

(52) U.S. Cl.
CPC .............. *A61N 1/3752* (2013.01); *H01R 13/02* (2013.01); *A61N 1/36071* (2013.01); *H01R 13/514* (2013.01); *H01R 13/5224* (2013.01); *H01R 2201/12* (2013.01)

(58) Field of Classification Search
CPC ............... A61N 1/3752; H01R 13/514; H01R 13/5224; H01R 2201/12
USPC ...................................... 439/909; 607/36–38
See application file for complete search history.

(56) References Cited

U.S. PATENT DOCUMENTS

| | | | |
|---|---|---|---|
| 4,469,104 A | 9/1984 | Peers-Trevarton | |
| 4,995,389 A | 2/1991 | Harris | |
| 5,545,188 A * | 8/1996 | Bradshaw et al. | ............... 607/37 |
| 5,795,165 A | 8/1998 | Jarl | |
| 5,899,930 A | 5/1999 | Flynn et al. | |
| 6,498,952 B2 * | 12/2002 | Imani et al. | ...................... 607/37 |
| 6,654,641 B1 | 11/2003 | Froberg | |
| 6,662,035 B2 | 12/2003 | Sochor | |
| 6,749,358 B2 | 6/2004 | Balsells | |
| 6,878,013 B1 | 4/2005 | Behan | |
| 6,895,276 B2 | 5/2005 | Kast et al. | |
| 6,895,876 B2 | 5/2005 | Bergere et al. | |
| 7,070,455 B2 | 7/2006 | Balsells | |

(Continued)

FOREIGN PATENT DOCUMENTS

| | | |
|---|---|---|
| DE | 19917779 | 11/2000 |
| EP | 1062986 | 12/2000 |

(Continued)

OTHER PUBLICATIONS

European Search Report; Date of Report: Apr. 17, 2013; Reference: PT02775EP; Applicant: Greatbatch Ltd.; Application No. EP 13151690.8-1652; Place of Search: Munich; Date of Completion of Search: Apr. 11, 2013.

(Continued)

*Primary Examiner* — George Evanisko (74) *Attorney, Agent, or Firm* — Pearne & Gordon LLP (57) ABSTRACT

A contact block for electrically connecting a medical device to a conductive pin using improved electrical contact components. More specifically, an electrical contact block for achieving electrical contact with a conductive portion of an in-line IPG pin by utilizing a plurality of spherical conductive contact structures arranged in a ring around the conductive portion of the pin and biased toward the pin and held in place using a compliant o-ring.

26 Claims, 7 Drawing Sheets

(56) References Cited

U.S. PATENT DOCUMENTS

| | | | |
|---|---|---|---|
| 7,195,523 B2 * | 3/2007 | Naviaux | 607/37 |
| 7,274,963 B2 | 9/2007 | Spadgenske | |
| 7,537,474 B2 | 5/2009 | Deininger et al. | |
| 7,654,843 B2 | 2/2010 | Olson et al. | |
| 7,690,953 B2 | 4/2010 | Boyd et al. | |
| 7,711,427 B2 | 5/2010 | Janzig et al. | |
| 7,769,458 B2 * | 8/2010 | Ries et al. | 607/37 |
| 7,890,175 B1 | 2/2011 | Rey et al. | |
| 8,131,370 B2 * | 3/2012 | Janzig et al. | 607/37 |
| 8,250,752 B2 * | 8/2012 | Drew | 29/857 |
| 8,504,172 B2 | 8/2013 | Chinn et al. | |
| 2003/0040780 A1 | 2/2003 | Haeg et al. | |
| 2003/0179536 A1 | 9/2003 | Stevenson et al. | |
| 2004/0167582 A1 | 8/2004 | Tvaska et al. | |
| 2006/0004419 A1 | 1/2006 | Olbertz | |
| 2006/0047322 A1 | 3/2006 | Naviaux | |
| 2007/0202728 A1 | 8/2007 | Olson et al. | |
| 2007/0208381 A1 | 9/2007 | Hill et al. | |
| 2008/0071320 A1 | 3/2008 | Brase | |
| 2008/0246231 A1 | 10/2008 | Sjostedt et al. | |
| 2008/0255631 A1 | 10/2008 | Sjostedt et al. | |
| 2009/0017668 A1 | 1/2009 | Deininger et al. | |
| 2009/0099620 A1 | 4/2009 | Rebentisch | |
| 2009/0118778 A1 | 5/2009 | Biggs, Jr. et al. | |
| 2009/0243756 A1 | 10/2009 | Stevenson et al. | |
| 2009/0258519 A1 | 10/2009 | Dilmaghanian et al. | |
| 2009/0312835 A1 | 12/2009 | Stevenson | |
| 2010/0016928 A1 | 1/2010 | Zdeblick et al. | |
| 2010/0109966 A1 | 5/2010 | Mateychuk et al. | |
| 2010/0191299 A1 * | 7/2010 | Ayzenberg | 607/2 |
| 2010/0274309 A1 | 10/2010 | Knipfer et al. | |
| 2011/0029036 A1 | 2/2011 | Yamamoto et al. | |
| 2011/0059639 A1 | 3/2011 | Dilmaghanian et al. | |
| 2011/0071593 A1 | 3/2011 | Parker et al. | |
| 2011/0137414 A1 | 6/2011 | Litzke et al. | |
| 2011/0184479 A1 | 7/2011 | Kast et al. | |
| 2011/0282410 A1 | 11/2011 | Lim | |
| 2012/0253424 A1 | 10/2012 | Smith et al. | |

FOREIGN PATENT DOCUMENTS

| | | |
|---|---|---|
| JP | 54057101 | 5/1979 |
| JP | 10223346 | 8/1998 |
| WO | 0064535 | 11/2000 |
| WO | 2005014108 | 2/2005 |
| WO | 2005105207 | 11/2005 |
| WO | 2011011223 | 1/2011 |
| WO | 2011017432 | 2/2011 |

OTHER PUBLICATIONS

Partial European Search Report; Application No. EP 15 15 7480; Place of Search: Munich; Date of Completion of Search: Apr. 30, 2015.

* cited by examiner

CONTACT BLOCK USING SPHERICAL ELECTRICAL CONTACTS FOR ELECTRICALLY CONTACTING IMPLANTABLE LEADS

FIELD OF THE INVENTION

This application relates generally to an electrical contact block for a medical device and, more specifically, to an electrical contact block for achieving electrical contact with an in-line IPG lead and utilizing spherical contact structures.

BACKGROUND OF THE INVENTION

Medical devices have been implanted in patients to perform a variety of tasks. For example, programmable pulse generating systems are used to treat chronic pain by providing electrical stimulation pulses from an epidural electrode array placed near a patient's spine. Such Spinal Cord Stimulation (SCS) is useful for reducing pain in certain populations of patients. SCS systems typically include one or more electrodes connected to one or more connectors of an External Pulse Generator (EPG) or an Implanted Pulse Generator (IPG) via leads. In the case of an EPG, the lead must be connected to the EPG via an exit from the body. The pulse generator, whether internal or external, generates pulses that are typically delivered to the dorsal column fibers within the spinal cord through the electrodes which are implanted along or near the dura of the spinal cord. In a typical situation, the attached leads exit the spinal cord and are tunneled around the torso of the patient to a subcutaneous pocket where the IPG is implanted, or the wires exit the patient for connection to the EPG.

U.S. Pat. Nos. 7,537,474 and 6,895,876, incorporated herein by reference, disclose a connector solution for an implantable pulse generator (IPG) utilizing a coiled spring inside a contact block. The ends of the spring are welded together yielding a torus shape through which the in-line lead is inserted. The spring coils cant to conform to the contact ring of an IPG lead, thus making electrical contact. Each coil which contacts both the lead and the block forms a separate redundant electrical contact.

However, the coiled springs used in the "toroidal spring in groove" devices are less than ideal, as the springs tend to be expensive and delicate, and thus easy to damage. These coiled springs also tend to be relatively difficult to keep in place due to the nature of such springs. Hence, an improved component for electrically contacting conductive portions of the in-line leads is desired.

SUMMARY OF THE INVENTION

Provided are a plurality of example embodiments of the invention, including, but not limited to, various designs for contact blocks having new electrical contacts for contacting conductive rings on insertable pins for use in contact assemblies for providing in implantable medical devices.

For example, provided is a contact block for a medical device comprising: a first component having a first interior portion and a first hole; a second component having a second interior portion and a second hole, wherein, the first interior portion and the second interior portion are arranged to form an interior space of the contact block, and wherein the first hole and the second hole form a contact block bore having an axis and of a size that is adapted for receiving a pin; at least one conductive contact provided within the interior space in a manner for contacting the pin; and a biasing component provided within the interior space for biasing each of the conductive contacts toward the axis for ensuring electrical contact between each of the conductive contacts and a conductive portion of the pin.

Also provided is a contact block for a medical device comprising: a first component having a first interior portion and a first hole; a second component having a second interior portion and a second hole, wherein, the first interior portion and the second interior portion are arranged to form an interior space of the contact block, and wherein the first hole and the second hole form a contact block bore having an axis and of a size that is adapted for receiving a pin; and a plurality of conductive contacts provided within the interior space around the axis in a manner for encircling the pin for contacting the pin.

Further provided is an contact block for a medical device comprising: a first component having a first interior portion and a first hole; a second component having a second interior portion and a second hole, wherein, the first interior portion and the second interior portion are arranged to form an interior space of the contact block, and wherein the first hole and the second hole form a contact block bore having an axis and of a size that is adapted for receiving a pin; plurality of conductive contacts provided within the interior space in a manner for encircling the pin; and a biasing component provided within the interior space for biasing each of the conductive contacts toward the axis for ensuring electrical contact between each of the conductive contacts and a conductive portion of the pin.

Also provided are any of the above contact blocks wherein the biasing component is an o-ring comprised of a compliant material.

Further provided are any of the above contact blocks wherein the first interior portion is a first groove, and wherein the second interior portion is a second groove, with the second groove being larger than the first groove, the second groove for receiving the biasing component.

Further provided are any of the above contact blocks wherein each one of the conductive contacts is a conductive sphere.

Further provided are any of the above contact blocks wherein the conductive contacts and the biasing component are sealed within the electrical component in a manner that prevents the conductive components from exiting the electrical component during use Also provided is an contact block for a medical device comprising: a first conductive component having a first interior portion and a first hole; a second conductive component having a second interior portion and a second hole, wherein, the first interior portion and the second interior portion are arranged to form an interior space of the contact block, and wherein the first hole and the second hole form a contact block bore having an axis and of a size that is adapted for receiving a pin; a plurality of conductive spheres provided within the interior space in a manner for encircling the pin; and an o-ring comprised of a compliant material that is provided within the interior space for biasing each of the conductive spheres toward the axis for ensuring contact with a conductive ring of the pin.

Further provided is a contact block for a medical device comprising: a first conductive component comprised of MP35N and having a first interior portion and a first hole; a second conductive component comprised of MP35N and having a second interior portion larger than the first interior portion and having a second hole, wherein, the first interior portion and the second interior portion are arranged to form an interior space of the contact block, and wherein the first hole and the second hole form a contact block bore having an axis and of a size that is adapted for receiving a pin of about 0.055 inches in diameter; a plurality of conductive spheres comprised of a conductive, low-corrosive metal and each being about 0.02 inches in diameter being provided within the interior space in a manner for encircling the entire circumference of the pin; and an o-ring comprised of a compliant material that is provided within the interior space in at the second interior portion for biasing each of the conductive spheres toward the axis for ensuring contact with a conductive ring of the pin.

Also provided is a contact assembly using any of the contact blocks provided above.

Further provided is an implantable medical device using any of the contact blocks provided above.

Also provided is a contact assembly for an implantable medical device comprising: a first stacker component forming an first interior open portion, the first stacker component having a first contact block receiving portion; a compliant insulating seal having a seal bore therethrough and being provided within the first interior open portion of the first stacker component; a contact block including; and a second stacker component having a second contact block receiving portion and a second bore.

The contact block of the contact assembly can be provided including a first conductive component having a first interior portion and a first hole, a second conductive component having a second interior portion and a second hole.

Furthermore, the above contact assembly can be provided where the first interior portion and the second interior portion are arranged to form an interior space of the contact block, and wherein the first hole and the second hole form a contact block bore having an axis and of a size that is adapted for receiving a pin, with a plurality of conductive contacts provided within the interior space in a manner for encircling the pin, and having a biasing component provided within the interior space for biasing each of the conductive contacts toward the common axis for ensuring contact between each of the conductive contacts and a portion of the pin.

The above contact assembly can be arranged for receiving the pin through the first stacker component, through the bore of the seal, through the contact block bore, and into the bore of the stacker second component, such that a conductive portion of the pin is provided in electrical contact with the conductive contacts when the pin is seated in the contact assembly.

Further provided is a stimulation system or method of providing stimulation using any of the above components or assemblies.

Also provided are additional embodiments of the invention, some, but not all of which, are described hereinbelow in more detail.

BRIEF DESCRIPTION OF THE DRAWINGS

The features and advantages of the examples described herein will become apparent to those skilled in the art to which this disclosure relates upon reading the following description, with reference to the accompanying drawings, in which.

DETAILED DESCRIPTION OF THE EXAMPLE EMBODIMENTS

Provided is a novel and unique way of achieving electrical contact with an in-line IPG lead pin utilizing a plurality of electrical conductive contacts provided in an interior space of a contact block, where the conductive contacts are for encircling an axially inserted pin that are biased toward the pin, in contrast to the widely utilized "toroidal spring in groove" concept discussed above in the background. This new approach can be adapted for use in at least some contact assemblies that were initially designed for use with the toroidal springs by merely replacing a single component with a similarly shaped component using the new contact design. The conductive contacts could be of spherical, cylindrical, or rectangular shapes, utilizing one or more biasing components such as an o-ring or gasket, or a plurality of individual biasing springs or compliant (e.g., rubber) mounts, for example.

Figure 1:
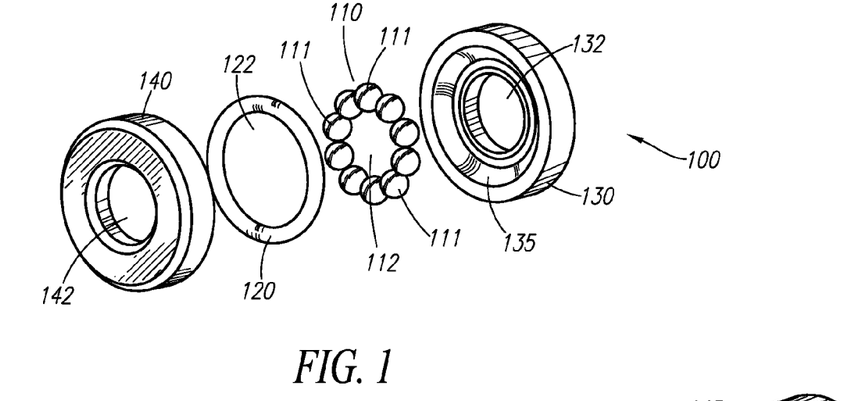
FIG. 1 is a diagram of an exploded view of a first example embodiment of a contact block having spherical conducive contacts formed in a ring.
Figure 1A:
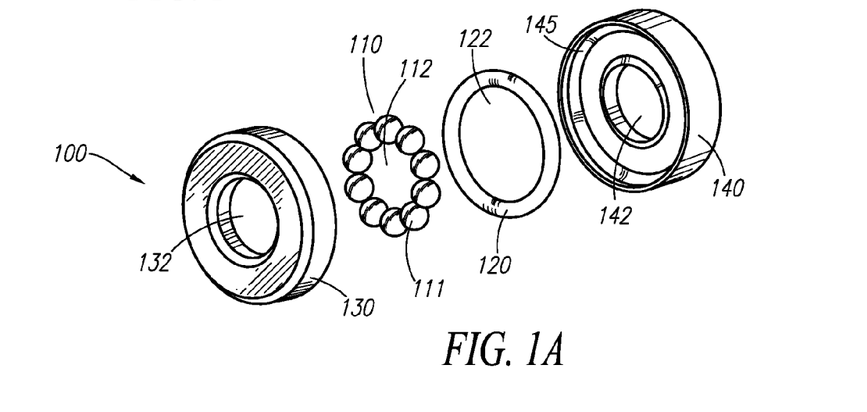
FIG. 1A another view of the example contact block of FIG. 1 rotated 180º.
Figures 2, 3:
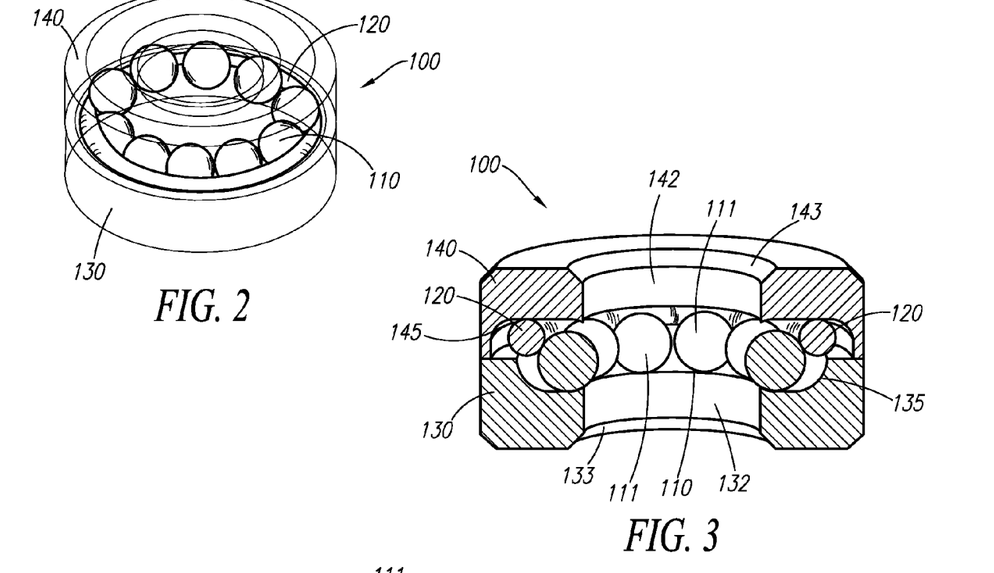
FIG. 2 is a transparent diagram of the ring portion of the example contact blocks of FIGS. 1 and 1B.
FIG. 3 is a cut-away diagram view of the ring portion of FIG. 2 cut axially.

FIG. 1 is a schematic diagram showing the primary components of an example embodiment of the contact block 100, while FIG. 2 shows the assembled contact block 100 in a "see-through" manner. FIG. 3 shows a cross section of the contact block cut along and bisecting its axis.

Figures 6, 7:
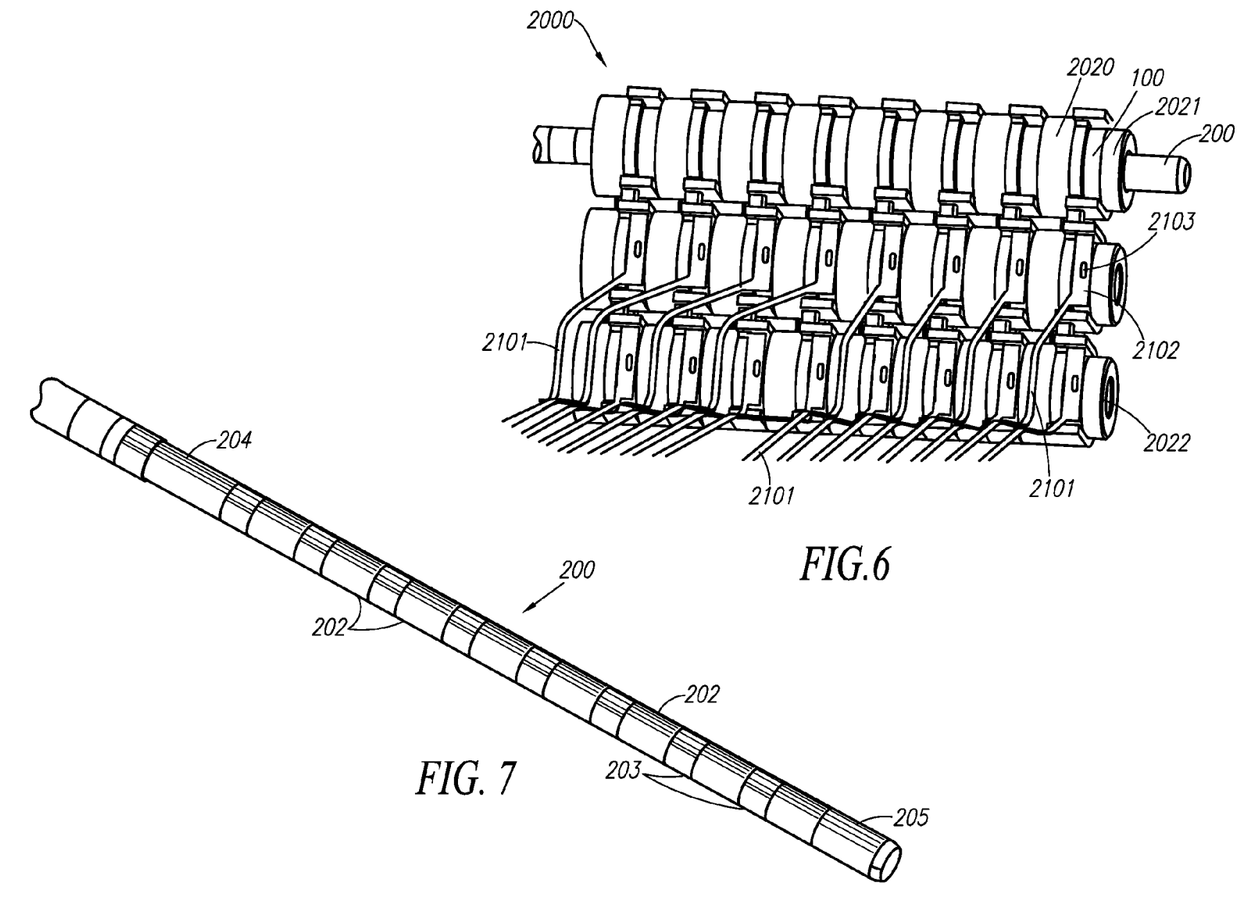
FIG. 6 is a diagram of primary components of a contact assembly comprising the example contact blocks of FIG. 1 with a subset of conductive leads attached and one IPG pin inserted therein.
FIG. 7 is a diagram of an example IPG pin.

The contact block 100 as shown in FIGS. 1, 1A, and 2-3 is comprised of a first contact block component 140 and a second contact block component 130 with respective holes 142, 132 for receiving an IPG lead pin (such an IPG lead pin is shown in FIG. 7). The second contact block component 130 has an interior groove 135 for receiving a conductive ring 110 that is comprised of a plurality of conductive spheres 111 arranged in a ring during assembly for forming ring 110 with hole 112. In this example, 10 conductive spheres 111 are used for the conductive ring 110, but other numbers of conductive spheres 111 can be utilized, based on their size and the desired application.

Figure 1B:
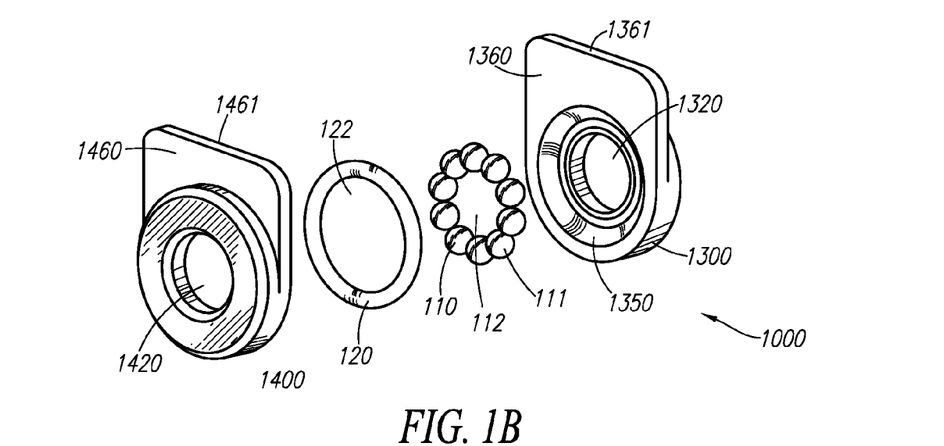
FIG. 1B is a diagram of an exploded view of a second example embodiment of a contact block having spherical conducive contacts formed in a ring.

The individual conductive spheres 111 are held in place after assembly by action of the groove 135 in combination with the flexible o-ring 120 with hole 122, but otherwise the spheres 111 forming the conductive ring 110 are not attached to each other, other than by mere physical contact, such as when the ring is compressed. This allows the conductive spheres 111 to move apart from, or toward, each other, allowing the conductive ring 110 to expand or contract in use, in particular in reaction to the insertion/removal of a pin 200. FIG. 1B shows these components in a reverse direction, showing interior groove 145 in the first contact block component 145 for holding the o-ring 120 and the conductive spheres 111 of the conductive ring 110 in place when assembled.

This new design uses the conductive spheres 111 as dynamic electrical contacts for contacting conductive portions of the respective IPG lead pins inserted through the contact block 100. Conductive contacts of shapes other than spheres could also be used. For example, one or more cylindrical or rectangular contacts could be used in place of the spheres, in particular where biasing components like springs are utilized (for example, an arrangement similar to a DC motor brush assembly could be utilized).

For the example embodiment, the conductive spheres 111 are kept in contact with the IPG pin inserted therein through action of the o-ring 120 and the interior grooves 135, 145. For this example embodiment, the contact block components 140,130 can be made from a conductive metal, such as, for example, MP35N (a commercially available nonmagnetic, nickel-cobalt-chromium-molybdenum alloy that has a unique combination of properties), although any conductive biocompatible metal or alloy could be used. The contact block components can be manufactured by using a metal injection molding (MIM) process, or machined using known machining methods. The conductive spheres 111 can be made from a conductive metal such as platinum, palladium, iridium, gold, or other implantable metal that is preferably of high electrical conductivity and low corrosive nature. Manufacturing techniques such as utilized for ball bearings might be used to form the spheres.

The contact block components 140, 130 are made with grooves 145,135 being slightly larger than the diameter of the conductive spheres 111. The grooves 145, 135 are also made large enough to allow the spheres 111 to move radially to accommodate the appropriate give and take to accept the IPG pin insertion. In the example embodiment, contact block 140 has interior groove 145 made slightly larger than interior groove 135 to accommodate the o-ring and the conductive spheres 111, which further allows the o-ring to move radially.

After assembly, the o-ring resides in contact block half 140. This allows the o-ring to apply an inward radial force on the spheres 111 and at the same time a "downward" axial force on the spheres 111 (into the groove 135). These forces ensure that the spheres 111 will remain in contact with conductive portion of the IPG lead pin (radial force) and also in contact with the contact block component halves (axial force) to ensure an adequate electrical contact from the conductive portion of the IPG pin to the contact block, and in particular in physical and electrical contact with contact block component 130. Thus, the o-ring 120 provides 2 vectored forces from a single part to ensure this desired electrical conductive path is maintained. These vectors can be adjusted for different applications by altering the thickness and outside diameter of the o-ring and by changing the durometer of the o-ring material, for example.

Thus, the inward radial forces determine the radial load that is applied to the conducting spheres as those spheres are pressed against the conducting portion of the IPG pin, and the downward axial force determines the load placed against the spheres and the contact block.

The grooves 135, 145 in the contact block component halves 130, 140 are designed to allow the spheres 111 and o-ring 120 as assembled to float radially, which allows the contacts to self-align for adequate conductive connectivity with the IPG pin and contact block. This float does not alter the contact forces between the spheres 111 and their respective contacts, however. The conducting spheres 111 are free to rotate, which increases robustness and ease of IPG pin insertion. The spherical shape also acts as a natural funnel for the IPG pin as it is inserted into the bore (holes 142, 122, 112, 132), of the contact blocks 100. The grooves 135, 145 are further designed such that the halves 130, 140, which are welded together when assembled with the contact spheres 111 and o-ring 120 therein, keep the internal components, i.e., the contact spheres 11 and o-ring 120, held in place to prevent them from spilling out of the contact block while it is handled, while it is being assembled into a device, and while it is in use with a pin 200 inserted therein.

For use in an example IPG device, such as the one described below, the diameter of the conductive spheres 111 are chosen to be about 0.02 inches because that is a commercially available size for electrical contacts in implantable precious metals, but the diameter can be adjusted based on other desired contact sizes. For this example, the o-ring 120 is comprised of an implantable grade of silicone rubber with a thickness of about 0.01 to 0.013 inches and an inside diameter of about 0.085 inches, which is also a standard size available in implantable grade material. This size o-ring maintains relatively low radial forces on the spheres, which are desirable for limiting IPG pin insertion forces.

The "o-ring" can also be of varied cross sectional shape; square, triangular, or obround for example. As discussed above, biasing components of other designs or materials could also be utilized. Springs, foams, or other structures could be utilized for biasing the conductive contacts, whether spheres or some other design.

After assembling the components in place, the contact block components 130, 140 are welded together to join the contact block 100, which ensures that the parts remain inside with little opportunity to come apart; a distinct advantage over the prior art product utilizing coil springs, since such springs can easily fall out (or spring out) of the components even after assembly, making transport and further assembly into an IPG more difficult.

The disclosed example designs can utilize standard sizes for the o-ring and spheres, which is a great benefit in lead times for manufacturing. The contact block halves are easily made on Swiss-type machines. The cost for the assembly is estimated to be half the cost of the available products. The design allows for virtually any size contact to be accommodated, from micro-sized to macro-sized, for application in a number of different products.

The IPG pin 200, such as shown in FIG. 7 as an example multi-contact IPG pin 200, as used in the industry that has a plurality of conductive portions on its surface, such as conductive rings 202 (8 are shown in the example) that are typically comprised of platinum, separated by insulating lead portions 203 and 205 (typically of a polymer insulating material). The pin has a setscrew ring 204 that is typically comprised of MP35N alloy for being set in a setscrew block using a corresponding set screw to hold it in place.

Figure 4:
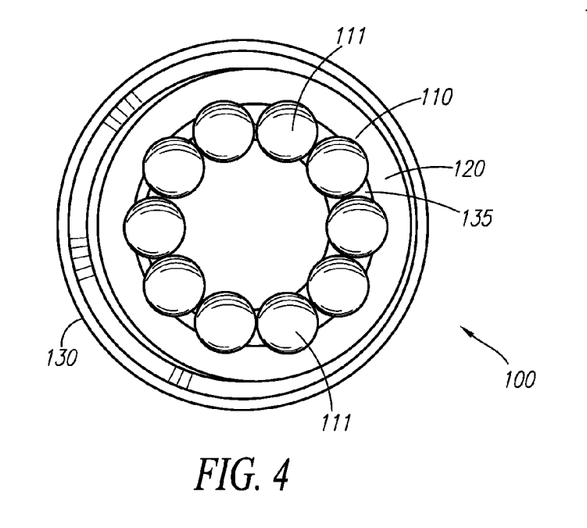
FIG. 4 is an internal diagram view of the ring portion of FIG. 2 with internal components that are out-of-place.
Figure 5:
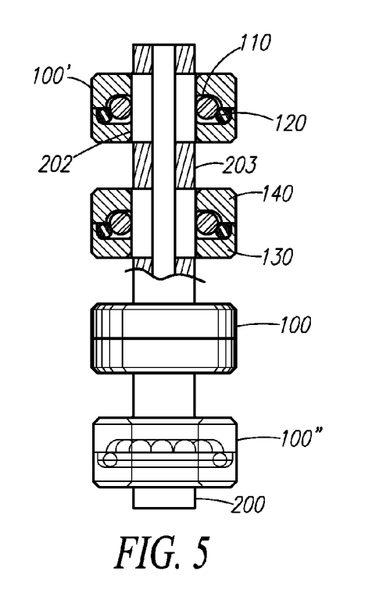
FIG. 5 has various views of the ring portion of FIG. 2 shown with an IPG pin inserted therethrough.

As shown in FIG. 5, the IPG pin 200, with conductive contact rings 202, can be inserted into the bore of the assembled contact block 100 (item 100' shows a cut-away view, whereas item 100" shows a see-through view of the contact block 100 with pin 200 inserted), where the spheres 111 are then forced radially outward, which allows the conductive ring 110 comprised of the spheres 111 to be self-sizing and self-aligning to ensure constant electrical contact with the IPG pin conductor rings 202. FIG. 4 shows an example contact block 100 with misaligned internal components that would be properly aligned upon insertion of the pin 200.

FIG. 6 shows an example assembled contact assembly 2000 using the contact blocks 100 for a 24 channel device. Each pin 200 (only one is shown inserted in the assembly 2000) carries 8 channels, and thus requires 8 contact blocks in a "column" and thus 3 pins for the 24 channels. Thus, three columns each with one bore to support one pin are provided. The contact blocks 100 are separated using stacker components 2020 formed of an insulative material. A set of three ends 2021 are provided to cap the final contact blocks 100 of each column, respectively. Twenty four leads 2101 (not all are shown) are provided to carry current from each of the contact blocks 100. The leads 101 are attached to a corresponding contact block using lead ends 2102 at the end of each of the leads 101. Each lead end 2102 is spot welded to the corresponding contact block 100 via weld spot 2103.

Figure 8:
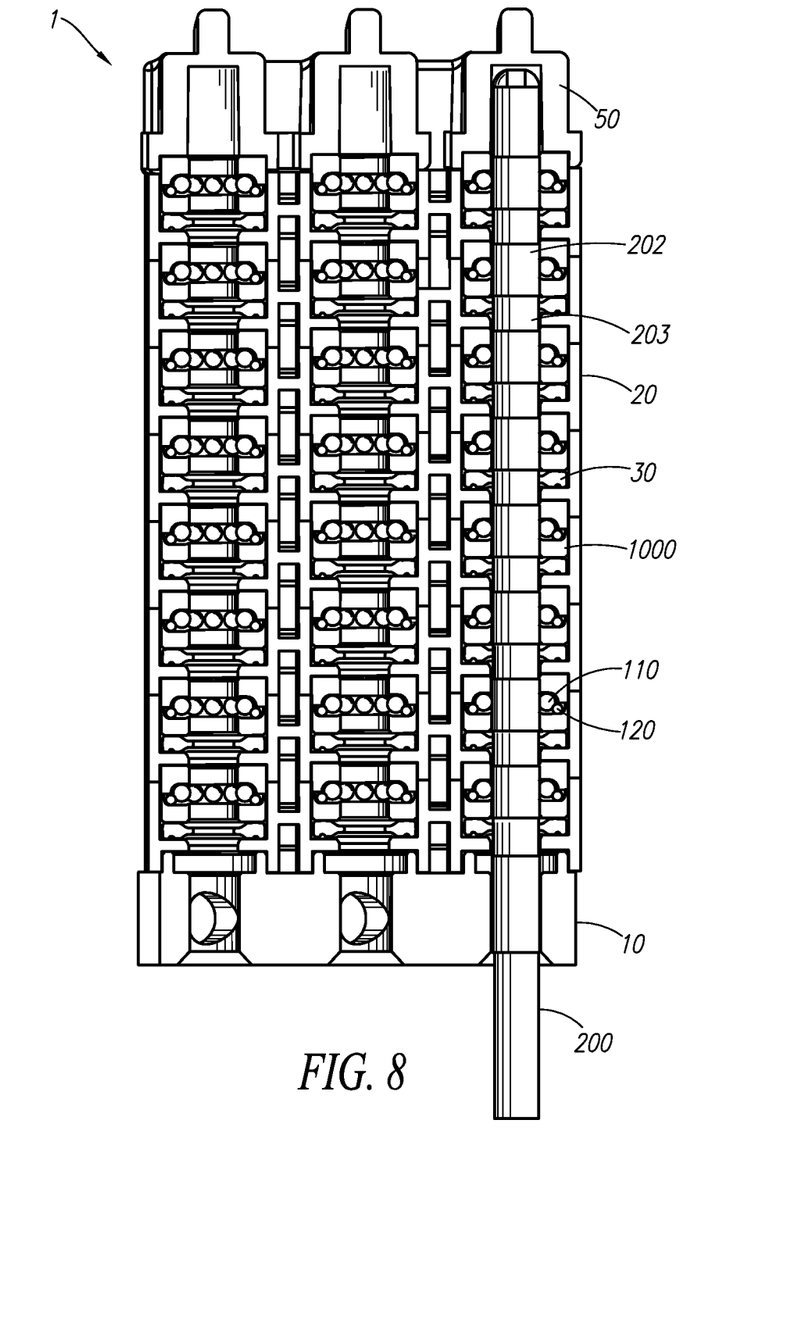
FIG. 8 is a cut-away view of the example contact assembly of FIG. 9.
Figure 9:
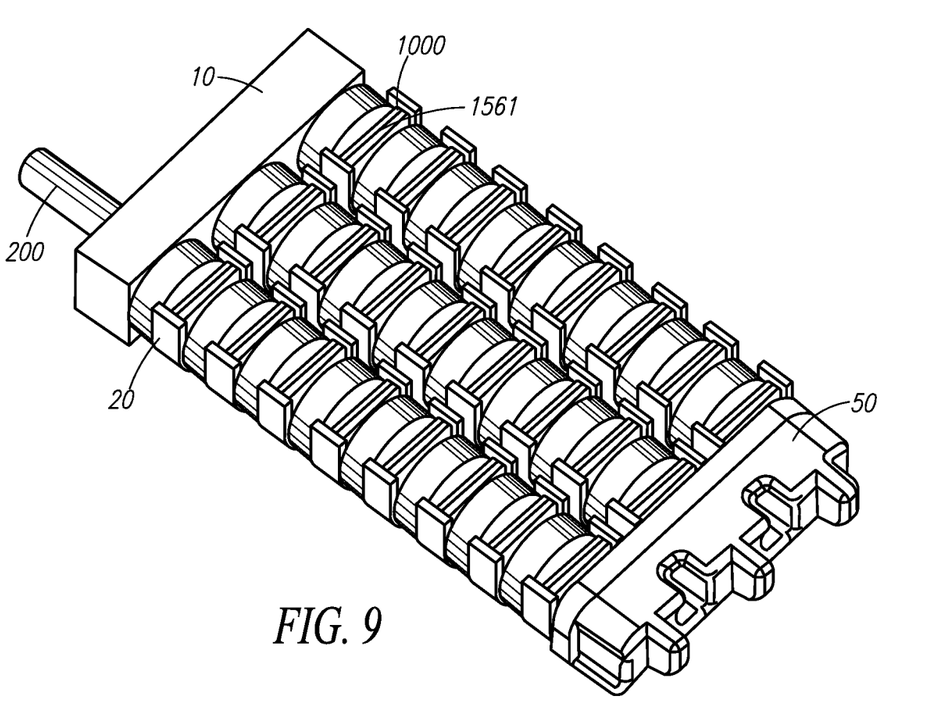
FIG. 9 a diagram of a contact assembly comprising the example contact blocks of FIG. 1B with one IPG pin inserted therein.

FIG. 9 shows another example assembled contact assembly 1 with one IPG pin 200 inserted using a contact block 1000 as shown in FIG. 1B, with FIG. 8 showing this example cut open to show the internal components. The contact block of FIG. 1B is comprised of the components of the example contact block of FIG. 1 and FIG. 1A, except that contact block components 130, 140 are replaced with contact block components 1300 and 1400 each having a respective contact tab 1360 and 1460 with respective contact surfaces 1361 and 1461 and respective holes 1320 and 1420 in order to comprise this additional example contact block 1000. One method of assembly of the contact block components 1300 and 1400 is to use the contact block components 130, 140 of the embodiment of FIG. 1 of the appropriate sizes, but modify them by fabricating them with tabs 1360, 1460 to the respective contact block components to obtain contact block components 1300 and 1400. In other aspects the assembly of the contact block 1000 is the same as that of the contact block 100. Or, the components 130, 140 can be manufactured with tabs 1360, 1460 integral thereto.

Contact block 1000 is provided with contact tabs 1360 and 1460 to make this contact block 1000 compatible with the contact assembly 1 as disclosed in U.S. patent application Ser. No. 13/081,836, incorporated herein by reference. In this manner, the contact block 1000 is a drop-in replacement for the contact block of that application that utilizes the coil spring of the prior art.

FIG. 8 shows a cut-away of this insertion process of FIG. 9, showing an example contact assembly 1 that is comprised of a setscrew block 10 and an end cap 50 covering opposite ends of the contact assembly. A plurality of polymer stacker components 20 are shown provided between the setscrew block 10 and the end cap 50. For this example embodiment, there is one stacker component 20 per "row". Each of the polymer stacker components is associated with a set of seals 30 and associated conductive contact blocks 1000 (three per row are shown in the example embodiment, representing three "columns", although other embodiments using 1, 2, 4, or other numbers of columns (i.e., other numbers of pin bores) can be supported) as described above. For this example embodiment shown in these figures, there are eight sets of stacker components 20 (i.e., forming 8 "rows") with each stacker component 20 (and thus each row) associated with a set of three contact block 1000/seal 30 groupings (i.e., three "columns"). Of course, alternative embodiments could utilize alternative numbers of stacker components 20 (i.e., different numbers of rows), and each stacker component might be associated with a different number of contact block/seal groupings (i.e., different numbers of columns), such as using a single grouping, or two, four, five, or more groupings, depending on the desired implementation. Alternatively, the stacker components could be comprised of separate sub-components each associated with one of the contact blocks (hence for the example, there would be three sub-components for each row).

The setscrew block 10 at one end is preferably comprised of titanium, although it could be comprised of any strong biocompatible metal such as stainless steel, nickel alloys, etc. The setscrew block 10 can be manufactured using a machining process, or a metal injection molding (MIM) process, for example. The setscrew block 10 holds setscrews (not shown) that tighten on the pins 200 setscrew rings and prevent the leads from moving out of alignment with the contacts and seals of the contact assembly. The setscrew block 10 has a set of three screws (not shown) that are used to set (fix) the pins 200 in place, once inserted, although other means of fixing the pins in place could be utilized, or the pins may be kept in place solely by friction contact with the seals and springs through which they pass, or by some other mechanism.

Each of the stacker components 20 is preferably comprised of a polymer such as Polysulfone, but it could be any biocompatible polymer or plastic or thermoplastic or other composition of similar capability. The stacker components 20 can be manufactured by using Injection molding, or a machining process suitable for its composition and size. The stacker components 20 hold the seals 30 and contact blocks 1000 in alignment (axially and radially), control seal compression, and act as a precision spacer to maintain contact to contact pitch. In the example embodiment, the stack pitch is about 0.100" nominal and accepts a pin of about 0.055" nominal diameter. The tolerance in the stacker contributes to the overall stack tolerance, likewise each of the seals is can be compressed as a separate assembly, so compression is controlled by the tolerances in one contact block and one seal not by the stack in its entirety.

The end cap 50 at the other end of the contact assembly 1 is preferably comprised of the same or similar material discussed for the stacker components 20. Alternatively, the end cap 50 could be comprised of a biocompatible metal with the inclusion of additional seals to ensuring sealing, in particular where a conductive end cap might be desirable. The end cap 50 forms the end of the pin bores and the depth of the holes providing in the end caps (for receiving the end of the IPG pins 200) registers the location where the pins align with the rest of the stack.

Figure 10:
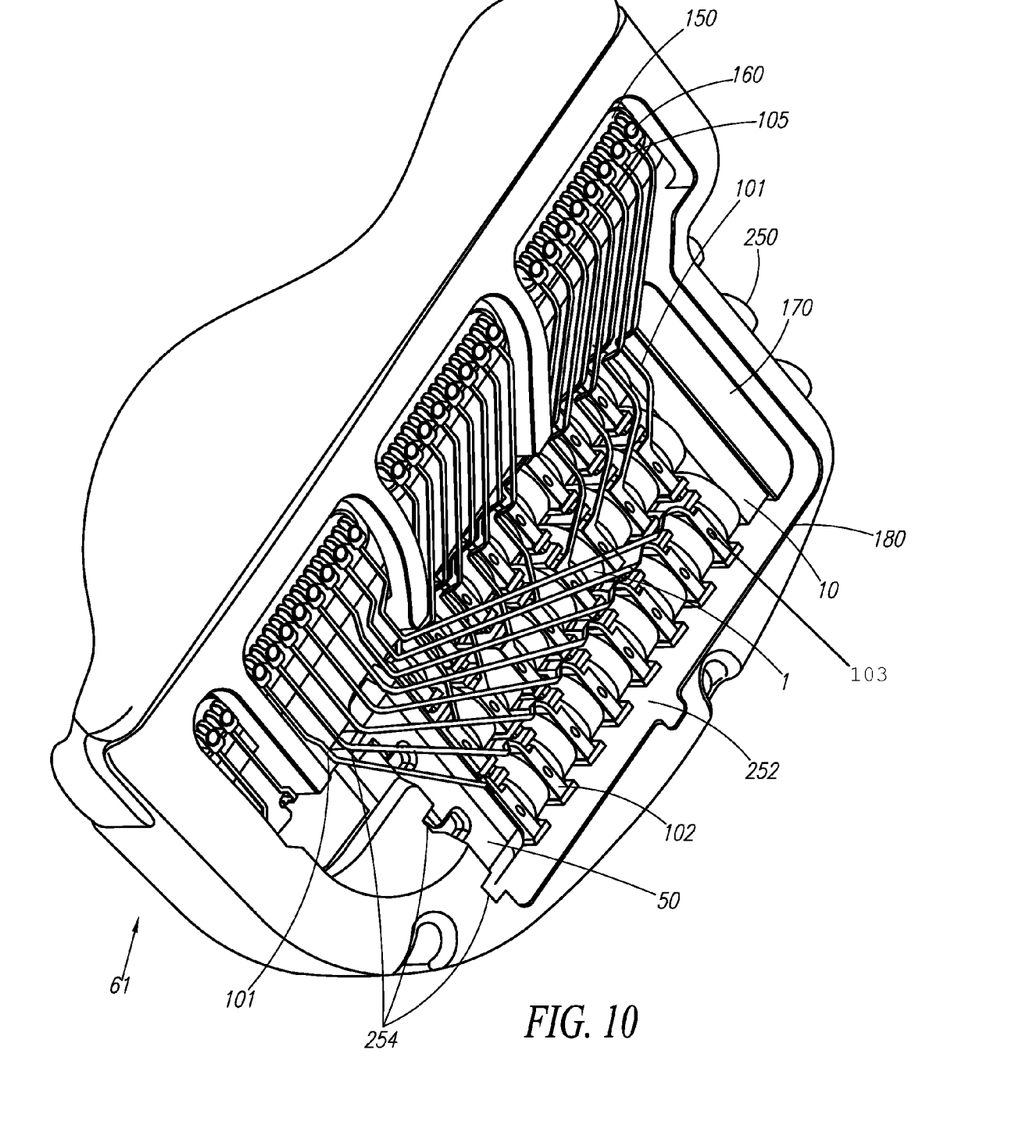
FIG. 10 is a partial diagram of an IPG including the example contact assembly of FIG. 9 electrically connected to the IPG via connecting leads.

As shown in FIG. 9, the flat portion 1561 of the contact block 1000 (comprised of the two contact surfaces 1361 and 1461 of the contact block halves 1300, 1400 that are welded together) protrudes from the stack and facilitates welding of an end of an electrically conductive lead or wire intended to route to/through a hermetic feed-through, as shown in FIG. 10. The stack and attached conductor wire 101 with end 102 is intended to be completely embedded in a nonconductive material such as thermoplastics, epoxy, or silicone. This nonconductive material is used to prevent fluid ingress into seams between the stackers.

The components are aligned to form an interlocking stack that prevents components from laterally separating, but longitudinally they can separate if left loose. Accurate positioning of seals and electrical contact locations in this arrangement is possible because the overall length tolerance of the stacker component is the only factor in end-to-end location variability. The stacker can be produced from a well centered micro-molding process that is capable of extremely tight tolerance control so that stacks consisting of as many as 12 contacts or more can be applied while maintaining acceptable accuracy. The contact assembly 1 allows medical devices, such as IPG devices, with multiple lead ports to have contact stacks that are assembled as a single unit and tested in a single fixture before assembly to determine that all channels have electrical continuity to an inserted pin that represents the connection end of a stimulation lead.

For the example embodiment shown in FIG. 10 for an IPG 61 using the contact assembly 1 utilizing the contact block 1000, the number of layers (rows) is chosen to be 8 (n=8), such that there are 8 rows (layers) of sets of 3 contact blocks placed in series, although any desired number of contact blocks could be accommodated by changing this arrangement (such as by using more or fewer layers and/or by having more or fewer than 3 blocks per row). Thus, in the example embodiment of FIG. 10, 24 contact blocks 1000 are provided for accommodating 24 connections, such as might be used in an IPG device having 24 channels (or 25 if the IPG case itself acts as a channel), for example. The choice of three sets of contact blocks (3 columns) in 8 serial rows are used to accommodate 3 IPG pins 200, with each IPG pin 200 having eight conductive rings 202, as shown in FIG. 7. Each of the IPG pins 200 in this example will therefore accommodate 8 separate conductive paths, such as to 8 electrodes, for example.

An alternative IPG could use only two sets of 12 contact blocks 1000 to also support a 24 channel device with two IPG pins of 12 channels each.

For the example embodiment of FIG. 10, three contact pins 200 can be inserted into the contact assembly 1, such as at cylinder bore 250. The entire contact assembly is arranged such that the insertion of the IPG pins 200 into the contact blocks 1000 (see FIG. 1B) cause a deformation of conductive ring 110 (e.g., slight expansion) held in place by the o-ring 120 to ensure a good electrical contact. The seals 30 (see FIG. 8) help to isolate and insulate the contacts from one another, including the prevention of fluids from providing an electrical path along the IPG pins 200. The stacker components provide a convenient means of stacking the contact blocks in a tight, organized and compact manner, and thus helps to hold the components tightly in place.

FIG. 10 shows the example IPG 61 utilizing the contact assembly 1 with all components assembled together. The connectors 105 of the contacts are electrically connected to the IPG internal components via connecting pins 160 on the IPG, using three lead frames to provide a total of 24 connections between the stack assembly and the IPG. Thus, the use of 3 pins of 8 contacts each will provide the possible connection of 24 electrodes to the IPG.

The assembled contact assembly 1 with pins therein is placed into a shell or housing 180. The shell has a feature (including the slots 254 of FIG. 10) that interlocks with the end cap tabs 56 on one side, including a vertical wall that forms a hard stop for the end cap 50. The other side of the shell 180 has an elastomeric piece 170 through which the bores continue through the cylinders 250. Assembly pins are inserted through the cylinders 250 of the elastomeric piece 170 first, then the curved and angled surfaces of the shell 180 and end cap 50 allow the rest of the stack to be pushed into place. Now the contact stack is trapped in alignment between the hard stop at the end cap 50 and the elastomeric piece 170 which serves as a spring to hold the stack in compression. The assembly pins can then be removed. The shell can then be attached to the IPG (or possibly was pre-attached). Then the lead frames 100 are attached to the IPG and the contact blocks, with the leads 101 being welded (preferable) or soldered to the contact tab 43 at weld/solder point 103 (see FIG. 6). Then the shell is filled with a potting material 252, such as silicone, for example, the potting material 252 surrounds the contact assembly and each of the leads and the IPG connection points to insulate the contact assembly electrically and physically hold the components in alignment to one another and binds the assembly together.

Figure 11:
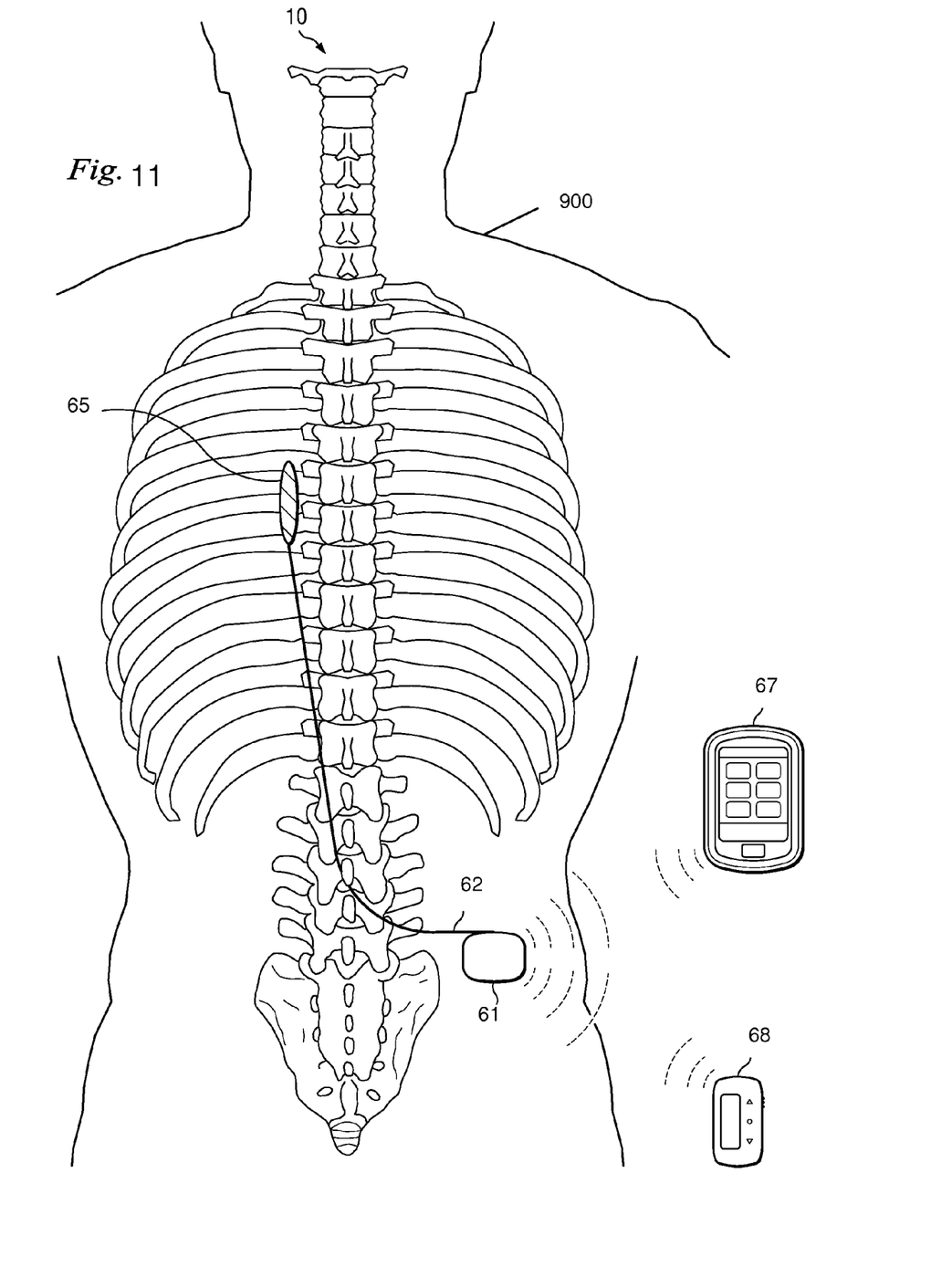
FIG. 11 is an illustration of an example medical application of an IPG that can use contact blocks as disclosed herein.

FIG. 11 shows an example application of the stimulator system for providing spinal stimulation to a patient 900. In that figure, the IPG 61 is shown implanted in a patient. The IPG 61 can be comprised of an internal power supply (that may include a rechargeable battery), a controller, pulse generation electronics, protection/conditioning circuits, and the contact assembly 1 for connecting to an electrode array. The IPG 61 can be supported by an external power supply (such as for charging the battery of the internal power supply), and a clinician programmer 67 and a user controller 68. Also shown is the human spine 10 with the stimulation Electrodes 65 are attached to the IPG 61 via electrode leads 62.

The leads and electrodes may be positioned anywhere along the spine to deliver the intended therapeutic effects of spinal cord electrical stimulation in the desired region of the spine. The distal end of the lead with its accompanying electrodes may be located along the epidural space and adjacent a desired portion of the spinal cord using well-established and known techniques for implanting and positioning SCS leads and electrodes, and the IPG 61 may be programmed using a clinician programmer 67 or other type of programmer 68 (such as a patient controller), as desired. The electrode leads 62 can be connected to the IPG via a contact assembly as described in this application.

Many other example embodiments can be provided through various combinations of the above described features. Although the embodiments described hereinabove use specific examples and alternatives, it will be understood by those skilled in the art that various additional alternatives may be used and equivalents may be substituted for elements and/or steps described herein, without necessarily deviating from the intended scope of the application. Modifications may be necessary to adapt the embodiments to a particular situation or to particular needs without departing from the intended scope of the application. It is intended that the application not be limited to the particular example implementations and example embodiments described herein, but that the claims be given their broadest reasonable interpretation to cover all novel and non-obvious embodiments, literal or equivalent, disclosed or not, covered thereby.

What is claimed is:

1. A contact block for a medical device comprising:
   a first component having a first surface forming a first groove encircling an axis of said contact block, a third surface extending from said groove, and a first hole;
   a second component having a second surface forming a second groove encircling said axis, and a second hole, wherein said second groove is wider than said first groove, said first groove and said second groove being arranged together about said axis to form a first interior space of said contact block such that said first surface and said second surface form an outer boundary of said first interior space about said axis, and wherein said third surface and said second surface form a second interior space, and wherein
   said first hole and said second hole form a contact block bore providing a second interior space of said contact block and having said common axis and of a size that is adapted for receiving a pin;
   at least one conductive contact provided at least partly within said first interior space outside of said second interior space and being arranged in a manner for contacting said pin when said pin is inserted into said second interior space; and a biasing component provided partially within said first interior space for biasing each of said conductive contacts toward said axis for ensuring electrical contact between each of said conductive contacts and a conductive portion of said pin.

2. The contact block of claim 1, wherein said biasing component is an o-ring comprised of a compliant material that is an electrical insulator.

3. The contact block of claim 2, wherein said compliant material is a natural or synthetic rubber.

4. The contact block of claim 1, wherein said second interior space is for receiving at least part of said biasing component.

5. The contact block of claim 1, further comprising an electrical weld for connecting said at least one conductive contact to an electrical lead.

6. A contact assembly for an implantable medical device comprising a plurality of the contact blocks of claim 1 organized in a series of rows and columns for utilizing a number of said pins each having a number of conductive portions such that the number of said pins is supported by the number of columns and wherein the number of conductive portions on each of said pins is supported by the number of rows.

7. The contact block of claim 1, wherein said first component and said second component are comprised of a conductive material.

8. The contact block of claim 7, wherein said conductive material includes MP35N.

9. A contact block for a medical device comprising:
a first component formed into a disc and having a first interior portion with a first inner surface, a third surface extending from said first inner surface, and a first hole;
a second component formed into a disc and having a second interior portion with a second inner surface wider than said first inner surface, and a second hole, wherein, said first interior portion and part of said second interior portion are arranged to form a first interior space of said contact block such that said first inner surface and part of said second inner surface form a boundary of said first interior space, and wherein said second inner surface forms a second interior space such that another part of said second inner surface and said third surface form a boundary of said second interior space, and further wherein said first hole and said second hole form a contact block bore providing a second interior space of said contact block and having an axis and of a size that is adapted for receiving a pin; and
a plurality of discrete conductive spheres provided at least partly within said first interior space but outside of said second interior space and being arranged around said axis in a manner for encircling said pin for contacting said pin.

10. The contact block of claim 9, further comprising a biasing component provided partly within said first interior space and partly within said second interior space for biasing each of said conductive contacts toward said axis for ensuring electrical contact between each of said conductive contacts and a conductive portion of said pin.

11. The contact block of claim 10, wherein said biasing component is an o-ring comprised of a compliant material.

12. The contact block of claim 9, wherein said conductive contacts are sealed within said electrical component in a manner that prevents said conductive contacts from exiting said electrical component during use or assembly into a device.

13. The contact block of claim 10, wherein said first interior portion is a first groove, and wherein said second interior portion is a second groove, with said second groove being wider than said first groove, said second groove for receiving said biasing component.

14. A contact block for a medical device comprising:
a first component having a first interior portion and a first hole;
a second component having a second interior portion and a second hole, wherein, said first interior portion and said second interior portion are arranged to form interior space around an axis of said contact block, and wherein said first hole and said second hole form a contact block bore around said axis and of a size that is adapted for receiving a pin;
a plurality of discrete conductive contacts provided within said interior space in a manner for encircling said pin such that said discrete conductive contacts are free to orbit around said axis; and
a non-conductive biasing component provided within said interior space for biasing each of said conductive contacts toward said axis for ensuring electrical contact between each of said conductive contacts and a conductive portion of said pin.

15. The contact block of claim 14, wherein said first interior portion is a first groove, and wherein said second interior portion is a second groove, with said second groove being circumferentially larger than said first groove, said second groove for receiving said biasing component.

16. The contact block of claim 14, wherein said conductive contacts are sealed within said electrical component in a manner that prevents said conductive contacts from exiting said electrical component during use or assembly into a device.

17. A contact block for a medical device comprising:
a first conductive component formed into a disc and having a first interior portion and a first hole;
a second conductive component formed into a disc and having a second interior portion wider than said first interior portion and a second hole, wherein said first interior portion and a first part of said second interior portion are arranged to form a first interior space of said contact block, and wherein another part of said second interior portion without any of said first interior portion forms a second interior space thinner than said first interior space, and further wherein said first hole and said second hole form a contact block bore having an axis and of a size that is adapted for receiving a pin;
a plurality of conductive spheres provided within said first interior space outside of said second interior space in a manner for encircling said pin; and
an o-ring comprised of a compliant material that is provided partly within said first interior space with the remainder within said second interior space and placed in contact with said conductive spheres for biasing each of said conductive spheres toward said axis for ensuring contact with a conductive ring of said pin.

18. The contact block of claim 17, wherein the conductive spheres are chosen to be about 0.02 inches in diameter.

19. The contact block of claim 18, wherein the o-ring is comprised of an implantable grade of silicone rubber with a thickness of between about 0.01 to 0.013 inches and an inside diameter of about 0.085 inches.

20. The contact block of claim 17, wherein the o-ring is comprised of an implantable grade of silicone rubber with a thickness of between about 0.01 to 0.013 inches and an inside diameter of about 0.085 inches.

21. A contact block for a medical device comprising:
a first conductive component formed into a disc comprised of MP35N and having a first groove and a first hole;
a second conductive component formed into a disc comprised of MP35N and having a second groove wider than said first groove and having a second hole, wherein, said first interior portion and a part of said second interior portion are arranged to form a first interior space around an axis of said contact block such that the remainder of said second interior portion forms a second interior space around the axis axially further from said axis than said first interior space, and wherein said first hole and said second hole form a contact block bore around said axis and of a size that is adapted for receiving a pin of about 0.055 inches in diameter;
a plurality of conductive spheres comprised of a conductive, low-corrosive metal and each being about 0.02 inches in diameter provided at least partly within said first interior space and outside of said second interior space in a manner for encircling the entire circumference of said pin; and
an o-ring comprised of a compliant material that is provided partly within said first interior space with a remainder within said second interior space and arranged to be in contact with said conductive spheres for biasing each of said conductive spheres toward said axis for ensuring contact with a conductive ring of said pin.

22. A contact block for a medical device comprising:
a first conductive component having a first interior portion formed from a first groove encircling an axis, a first inner surface, and a first hole;
a second conductive component having a second interior portion formed of a second groove encircling said axis having a larger circumference than said first groove, a second inner surface, and a second hole, wherein, said first groove and said second groove are each arranged to form a part of a boundary forming a first interior space of said contact block, and wherein said first hole and said second hole form a contact block bore providing a second interior space of said contact block, said bore having said axis and of a size that is adapted for receiving an inserted pin;
a plurality of conductive spheres provided at least partly within said first interior space in a manner configured for encircling the inserted pin, said conductive spheres being arranged such that said conductive spheres may orbit around said common axis within said first interior space, said plurality of conductive spheres also having a portion entering said second interior space for contacting the inserted pin; and
an o-ring including an insulating material and being provided within said interior space primarily in the second interior portion, said o-ring having a surface placed in contact with said plurality of conductive spheres for biasing each of said conductive spheres toward said common axis for ensuring contact between each of said conductive spheres and a portion of said inserted pin.

23. A contact block for a medical device comprising:
a first conductive component having a first interior portion and a first hole;
a second conductive component having a second interior portion and a second hole, wherein, said first interior portion and said second interior portion are arranged to form an interior space of said contact block, and wherein said first hole and said second hole form a contact block bore having an axis and of a size that is adapted for receiving a pin;
a plurality of conductive spheres provided within said interior space in a manner for encircling said pin, wherein the conductive spheres are chosen to be about 0.02 inches in diameter; and
an o-ring comprised of a compliant material that is provided within said interior space for biasing each of said conductive spheres toward said axis for ensuring contact with a conductive ring of said pin, wherein
the o-ring is comprised of an implantable grade of silicone rubber with a thickness of between about 0.01 to 0.013 inches and an inside diameter of about 0.085 inches.

24. A contact block for a medical device comprising:
a first component having a first surface forming a first groove encircling an axis of said contact block, a third surface extending from said groove encircling the axis further from said axis than said first surface, and a first hole;
a second component having a second surface forming a second groove wider than said first groove encircling said axis, and a second hole, wherein, said first groove and part of said second groove are arranged together about said axis to form a first interior space of said contact block such that said first surface and said second surface form an outer boundary of said first interior space about said axis, and wherein another part of said second groove forms a second interior space such that part of said second surface and said third surface form a boundary of said second interior space, and further wherein
said first hole and said second hole form a contact block bore providing a second interior space of said contact block and having said common axis and of a size that is adapted for receiving a pin;
at least one conductive contact provided at least partly within said first interior space outside of said second interior space and being arranged in a manner for contacting said pin when said pin is inserted into said second interior space; and
a biasing component separate from said first component and said second component, said biasing component adapted to be provided within part of said first interior space and part of said second interior space for biasing said at least one conductive contact toward said axis for ensuring electrical contact between each of said conductive contacts and a conductive portion of said pin.

25. The contact block of claim 24, wherein said biasing component is an o-ring comprised of a compliant material that is an electrical insulator.

26. A contact block for a medical device comprising:
a first component having a first partly curved surface forming a first groove encircling an axis of said contact block, a third flat surface extending from said groove, and a first hole;
a second component having a second partly curved surface forming a second groove encircling said axis, and a second hole, wherein, said first groove and part of said second groove are arranged together about said axis to form a first interior space of said contact block such that said first surface and part of said second surface form an outer boundary of said first interior space about said axis, and wherein said third surface and a part second surface including said curve form an outer boundary of a second interior space, and further wherein said first hole and said second hole form a contact block bore providing a second interior space of said contact block and having said common axis and of a size that is adapted for receiving a pin;

at least one conductive contact provided at least partly within said first interior space and being arranged in a manner for contacting said pin when said pin is inserted into said second interior space; and a compliant o-ring configured for being provided at least partly within said second interior space for biasing each of said conductive contacts toward said axis for ensuring electrical contact between each of said conductive contacts and a conductive portion of said pin.

* * * * *